(12) United States Patent
Paterno

(10) Patent No.: US 7,301,463 B1
(45) Date of Patent: Nov. 27, 2007

(54) ASSISTING AND MONITORING METHOD AND SYSTEM

(75) Inventor: David Joseph August Paterno, State College, PA (US)

(73) Assignee: Sage Life Technologies, LLC, State College, PA (US)

( * ) Notice: Subject to any disclaimer, the term of this patent is extended or adjusted under 35 U.S.C. 154(b) by 84 days.

(21) Appl. No.: 11/104,765

(22) Filed: Apr. 13, 2005

Related U.S. Application Data

(60) Provisional application No. 60/639,098, filed on Dec. 27, 2004, provisional application No. 60/521,379, filed on Apr. 14, 2004.

(51) Int. Cl.
  *G08B 23/00* (2006.01)
(52) U.S. Cl. ............... 340/573.1; 340/522; 340/309.7
(58) Field of Classification Search ............... 340/500, 340/502, 505, 506, 531, 539.1, 539.11, 539.14, 340/286.01, 286.06, 573.1, 573.5, 521, 522, 340/309.4, 309.7, 309.8, 286.07; 370/352; 379/37; 725/76; 705/34; 600/300, 301; 128/903, 904, 920, 921
See application file for complete search history.

(56) References Cited

U.S. PATENT DOCUMENTS

| | | | |
|---|---|---|---|
| 6,349,289 B1 * | 2/2002 | Peterson et al. | 705/34 |
| 6,909,708 B1 * | 6/2005 | Krishnaswamy et al. | 370/352 |
| 7,100,187 B2 * | 8/2006 | Pierzga et al. | 725/76 |
| 7,130,383 B2 * | 10/2006 | Naidoo et al. | 379/37 |

* cited by examiner

*Primary Examiner*—Van T. Trieu
(74) *Attorney, Agent, or Firm*—Synnestuedt & Lechner LLP; Mark D. Simpson

(57) ABSTRACT

A convenient task reminder, compliance logging and monitoring system for routine activities is presented as well as an automated communications/notification system that can relay the activity and/or inactivity recorded by the Home Unit device to other systems and/or specifically designated people.

19 Claims, 14 Drawing Sheets

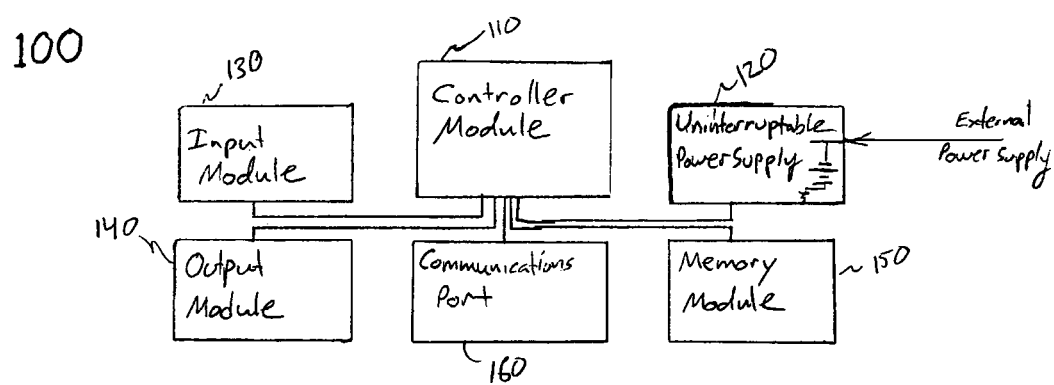

Figure 2 Home Unit Memory Record

200

| | |
|---|---|
| Event Schedule | ~210 |
| Message and Reminder Parameters | ~220 |
| Input Parameters | ~230 |
| Output Parameters | ~240 |

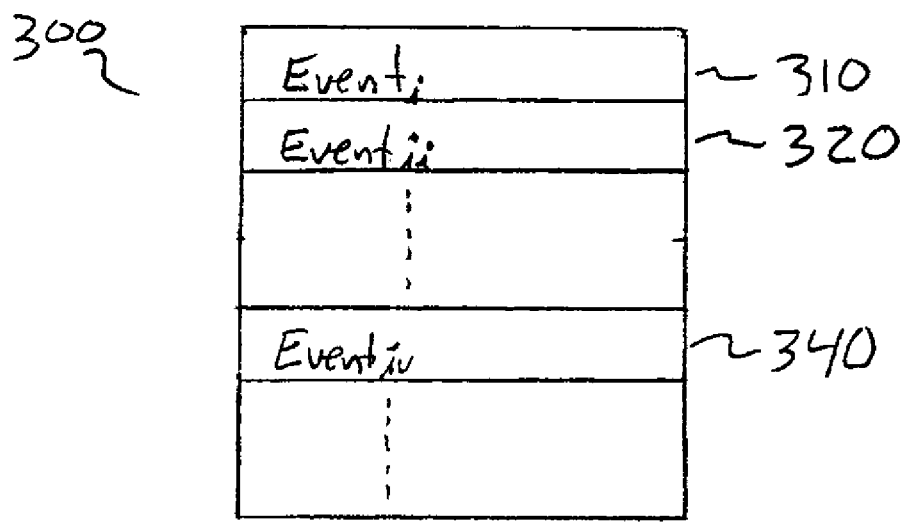

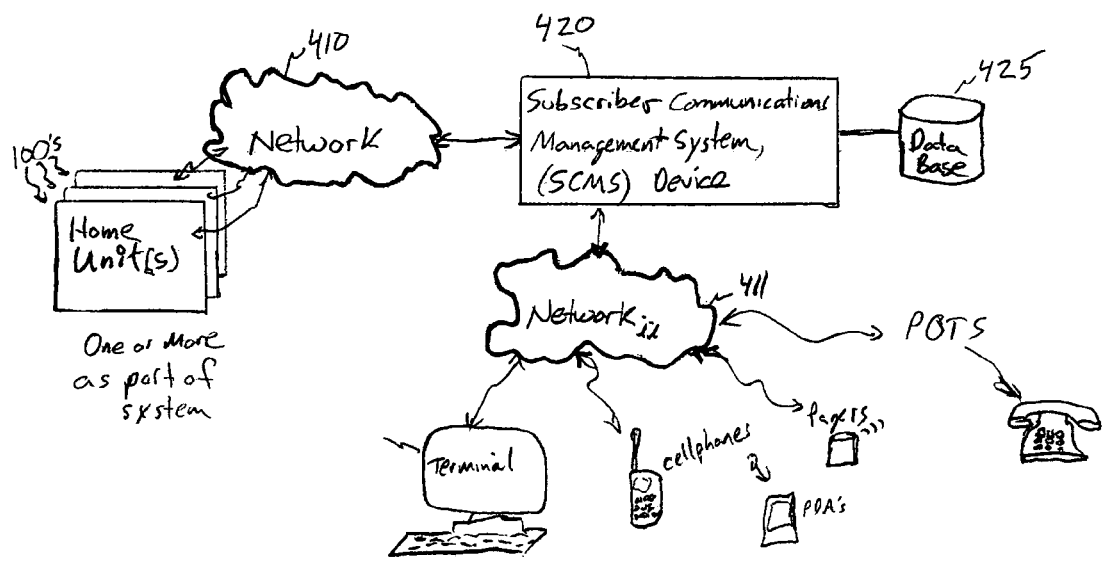
Figure 4 Reminder Logging & Notifying System

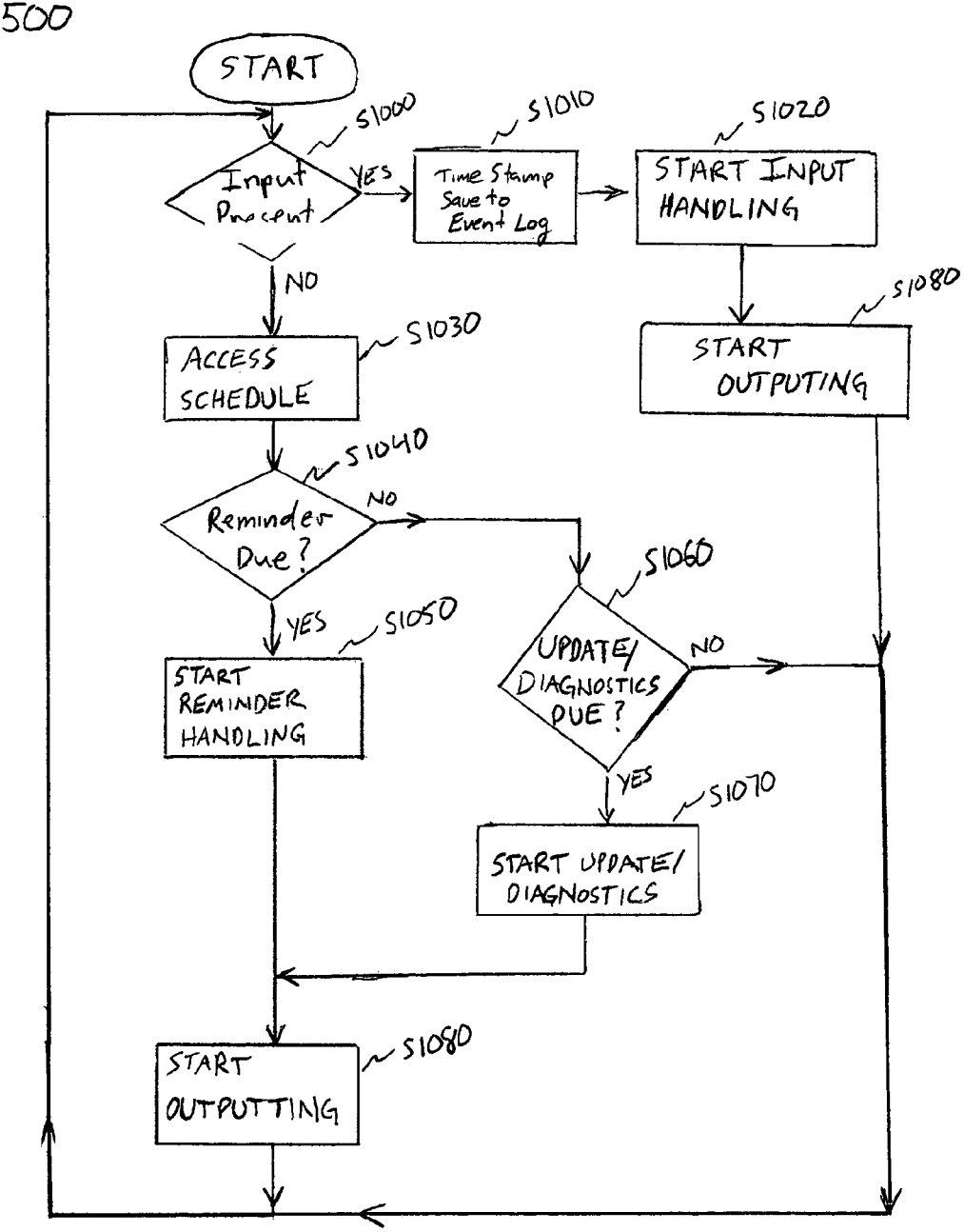

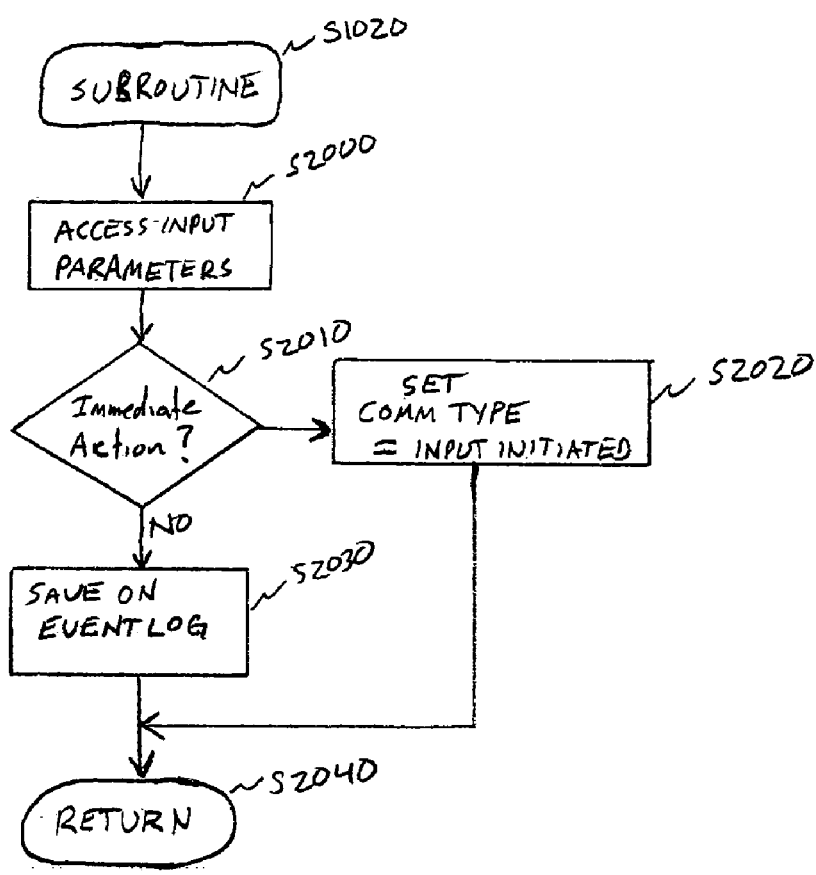

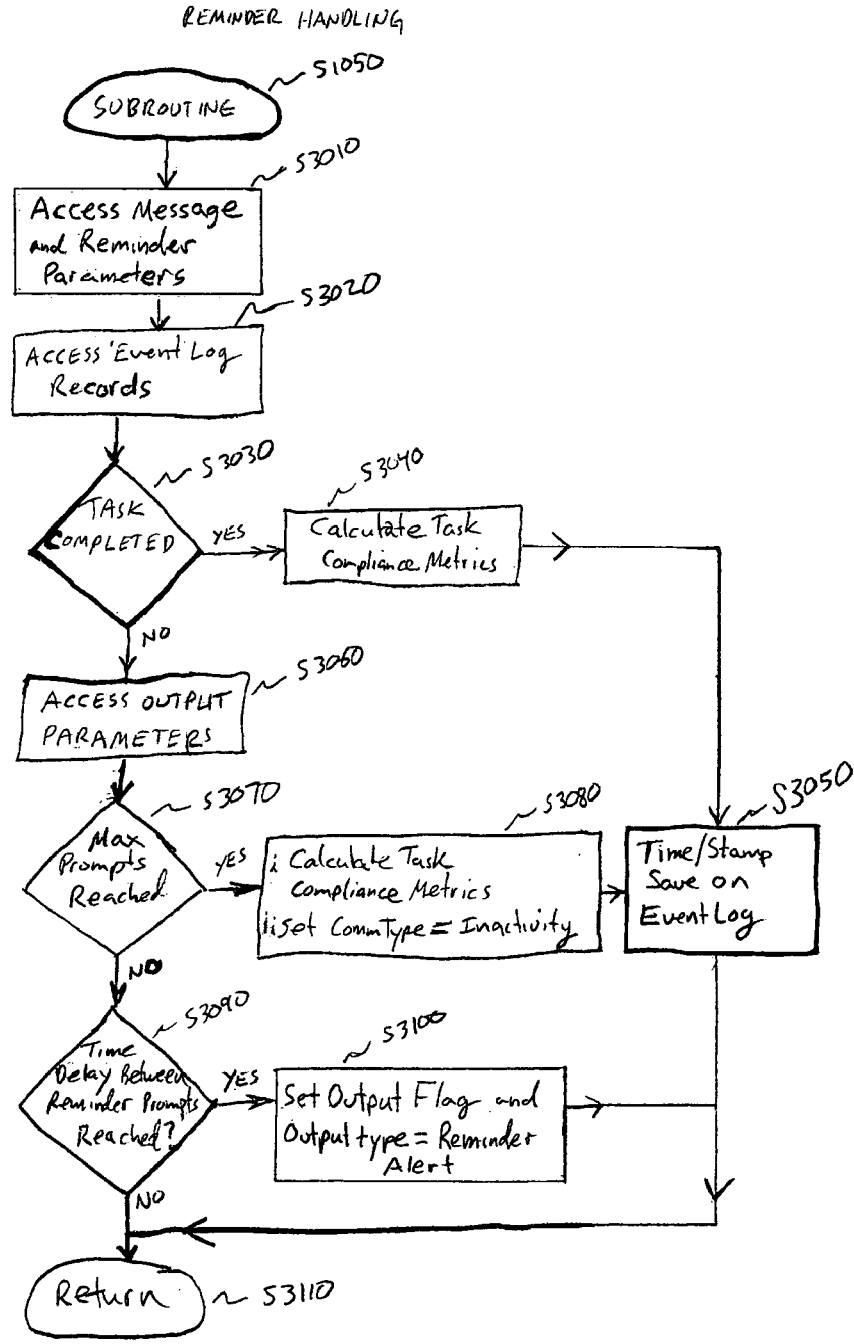

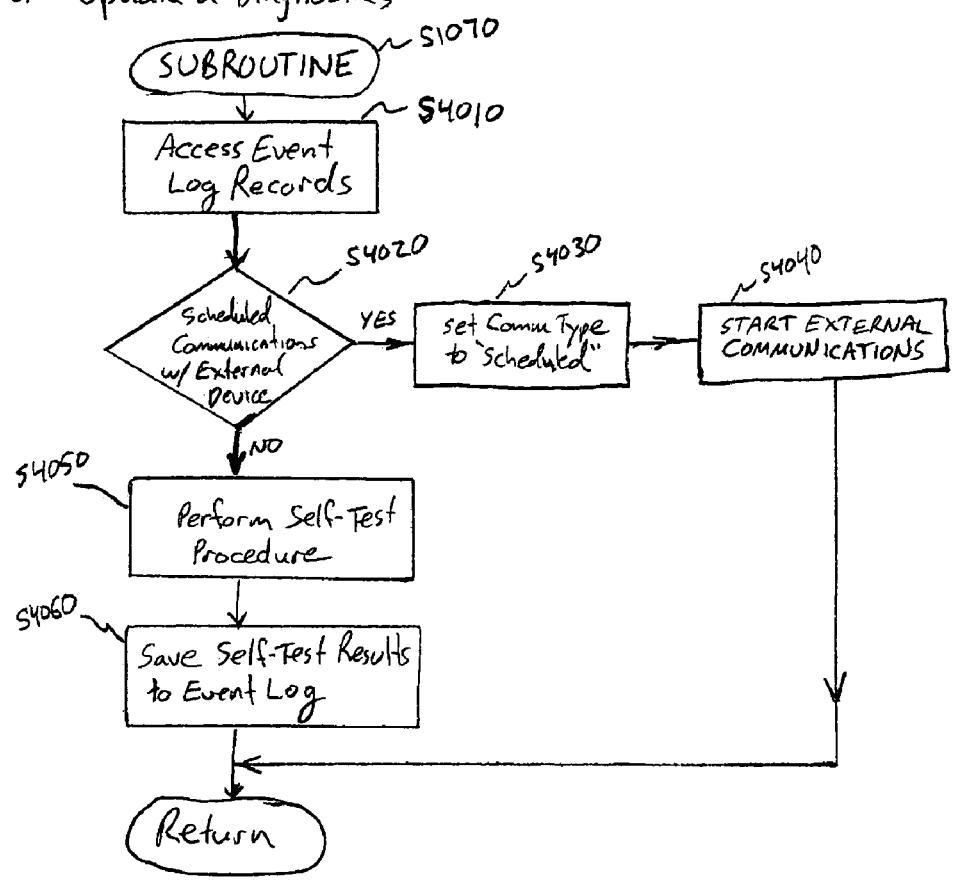

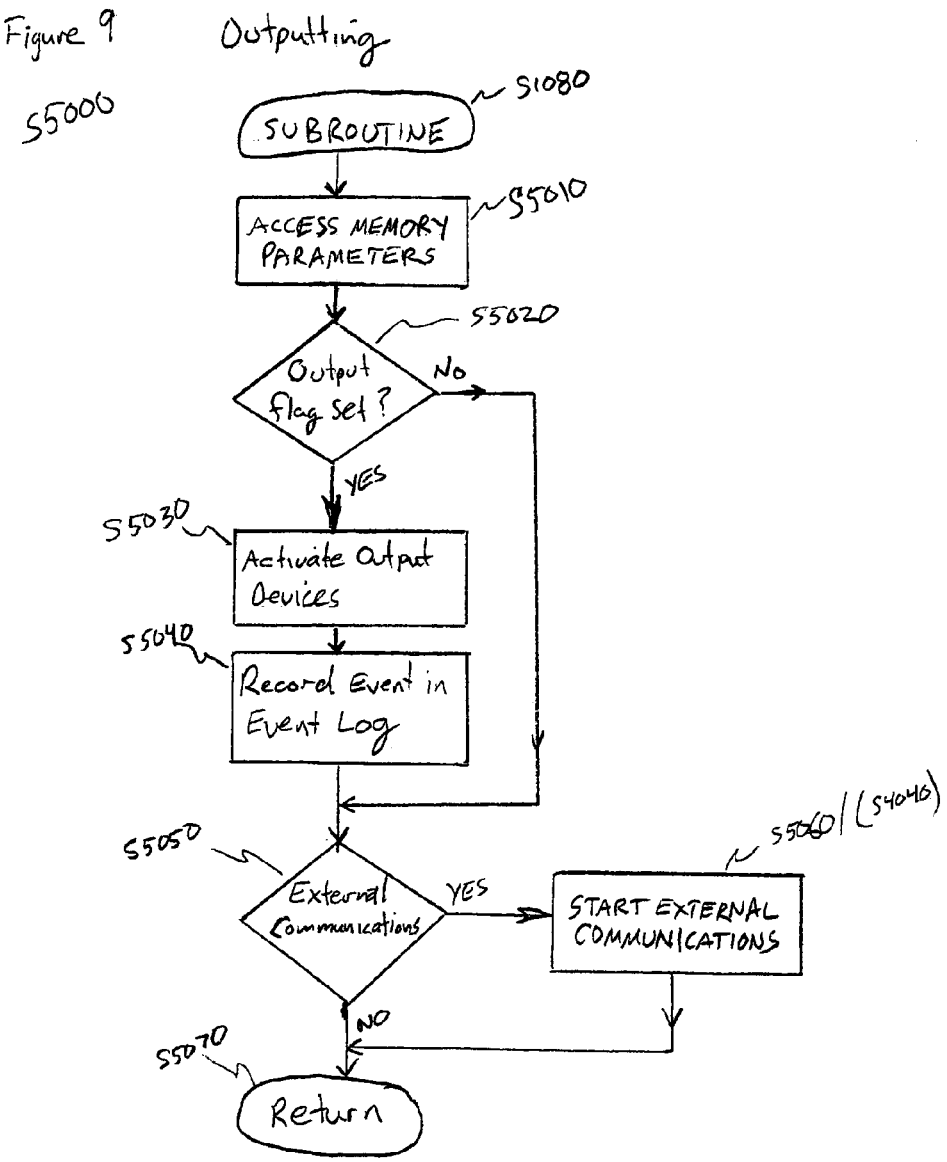

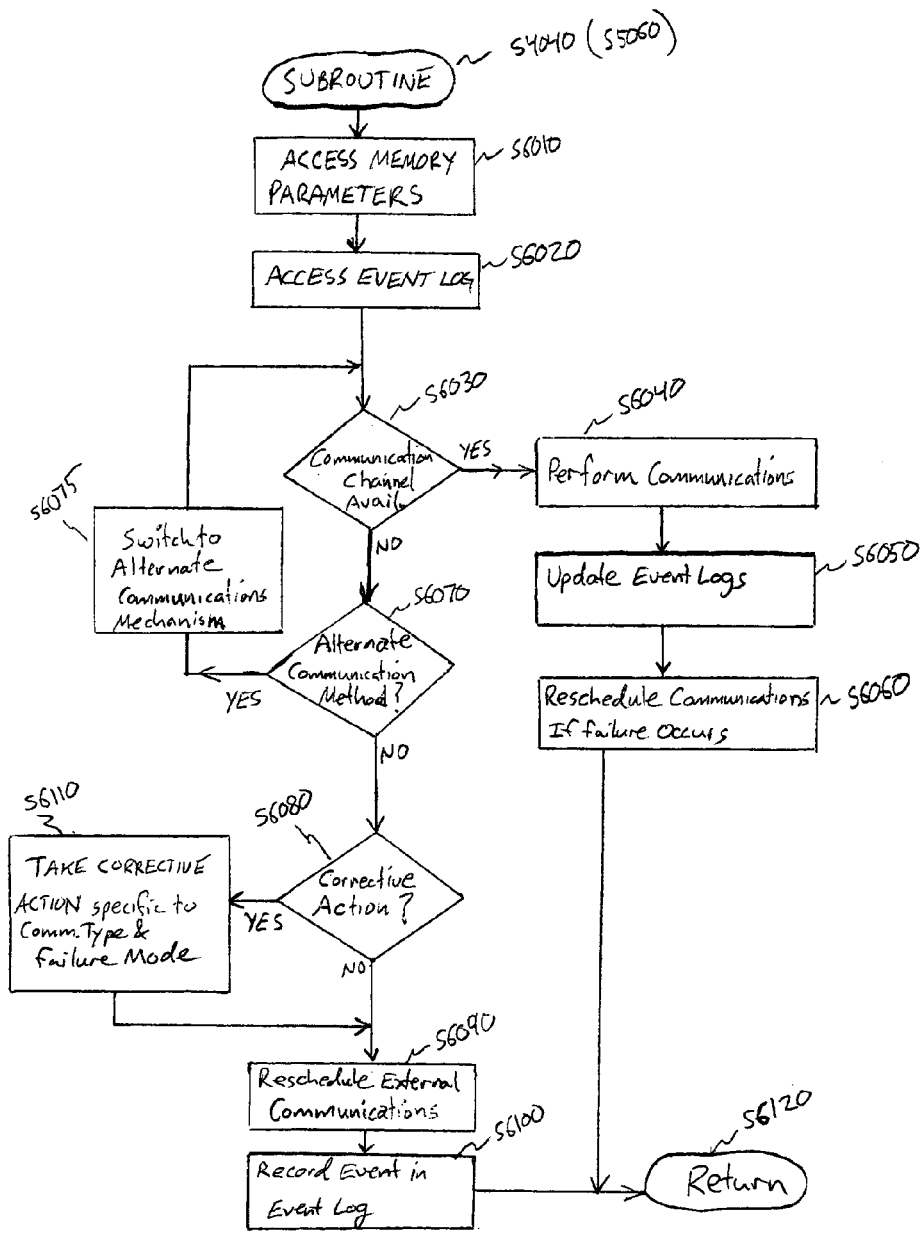

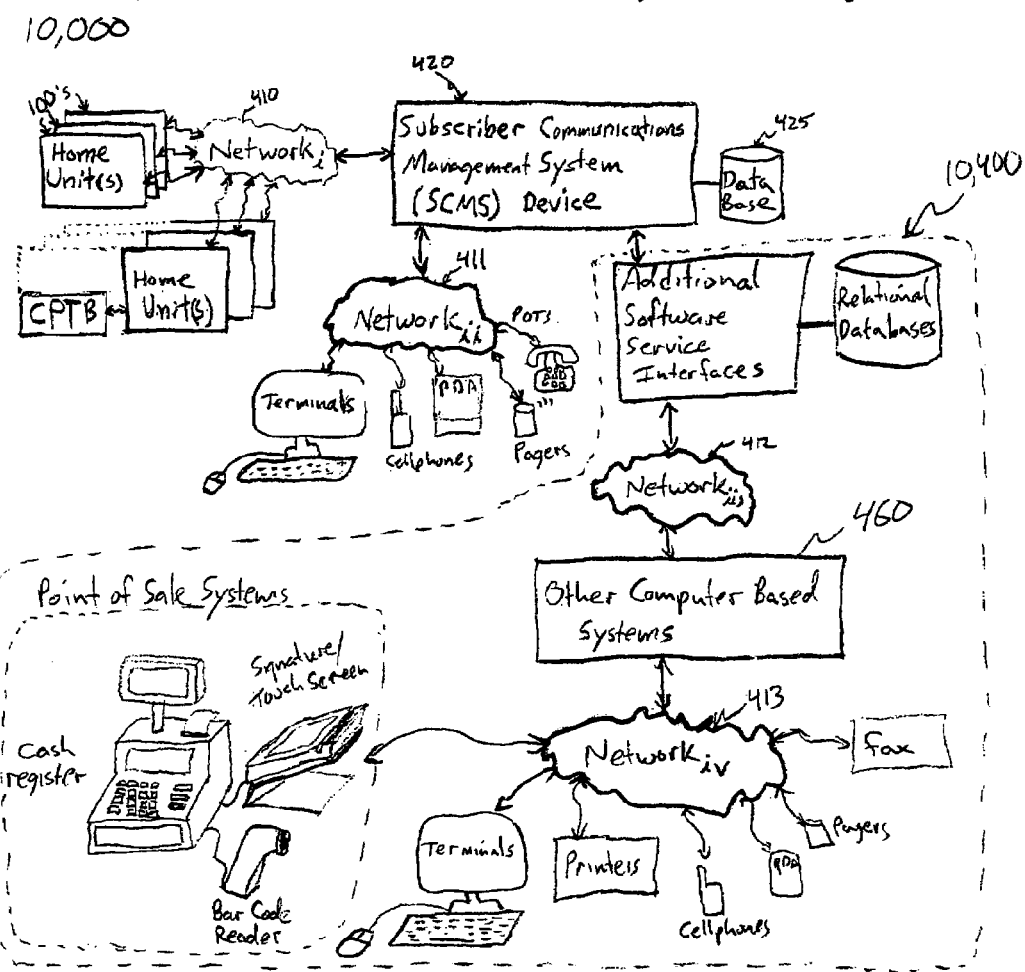
Figure 11 Expanded Reminder Logging and Notifying System

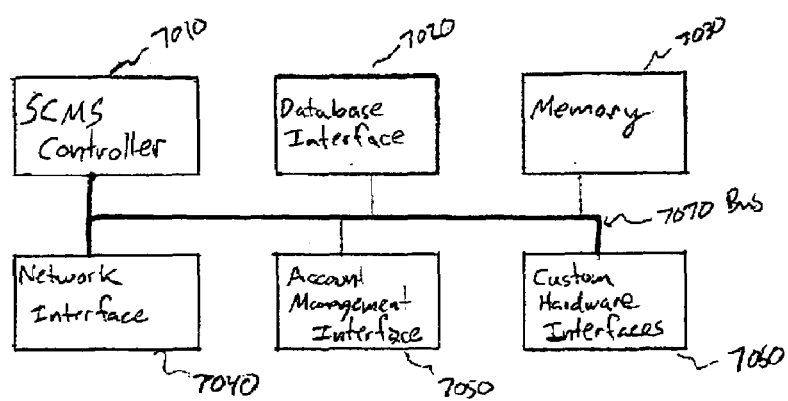
Figure 12 Block Diagram of Subscriber Communications Management System Device (SCMS)

Figure 13
8000

| | |
|---|---|
| Profile | —8010 |
| Profile | ~8020 |
| Profile | ~8030 |
| ⋮ | |
| Profile | ~8050 |
| ⋮ | |

Figure 14
9000

| | |
|---|---|
| Unique ID of Home Unit | ~9010 |
| Event Schedule | ~9020 |
| Reminder Contents | ~9030 |
| Communication Schedule | ~9040 |
| Account Member Info | ~9050 |
| Integrated Services Parameters | ~9055 |
| Notification Parameters | ~9060 |
| Home Unit Event Logs | ~9070 |
| Profile Specific SCMS Event Logs | ~9080 |

ASSISTING AND MONITORING METHOD AND SYSTEM

CROSS-REFERENCE TO RELATED APPLICATIONS

This application claims the benefit and priority of provisional applications, application No. 60/521,379, filed Apr. 14, 2004, and application No. 60/639,098 filed Dec. 27, 2004.

STATEMENT REGARDING FEDERALLY SPONSORED RESEARCH

Not Applicable.

REFERENCE TO A SEQUENCE LISTING, A TABLE, OR A COMPUTER

Not Applicable.

REFERENCES CITED

U.S. Patents Documents

| 6075755 | June, 2000 | Zarchan | 368/10 |
| 6359557 | March, 2002 | Bilder | 340/531 |

U.S. Patents Applications

| 20010026223 | October, 2001 | Menard et al. | 340/573.1 |
| 20030140021 | July, 2003 | Ryan et al. | 706/16 |

BACKGROUND OF THE INVENTION

This invention relates to providing convenience reminders, improving compliance to performing routine tasks, and providing automated communications between a person and his or her caregiver(s).

Monitoring devices and systems exist that can provide in home monitoring of critical health parameters such as blood sugar, pressure, heart rate and weight. These systems report the critical parameters to a remote health care professional and greatly aid in healthcare management of people with chronic illnesses. Other devices also exist that provide convenience reminders to help elderly people remember to perform daily tasks such as taking their self-tests and/or medications. These systems, however, do not provide an automated messaging service to the informal caregivers of the elderly person. Furthermore, a low cost Home Unit and communications tool is needed to empower the elderly person to perform his tasks and automatically send messages related to his activity to the common communication tools of informal caregivers. Such a system can further assist the individual by enabling other valuable services that are made possible by the presence of a Home Unit and a communications management service system.

OBJECTS AND SUMMARY OF THE INVENTION

An Assisting and Monitoring method and system for compliance logging and monitoring system for routine activities is presented as well as an automated communications/notification system that can relay the activity and/or inactivity recorded by a Home Unit device to other systems and/or specifically designated people.

The principle objective of the present invention is to provide reminders and messages to an individual, track the individual's responses to the reminders and messages, and relay the individual's responses to one or more other people. The primary purpose of which is to help an individual and select caregivers of the individual track the individual's performance of routine tasks.

Another objective of the present invention is to provide the other persons, (informal caregivers), a method to remotely set two-way interactive reminders and messages to be delivered to the said first person at set future times.

A further objective of the present invention is to provide the informal caregivers customizable settings for how and when they wish to receive interactive responses from their scheduled messages. The customization allowing for notifications to be dependent on the actual responses, or lack thereof.

An additional objective of the present invention is to provide select input conditions that the said first person can initiate, that may change the behavior the system will take with pending reminders, messages, and/or notification steps. For example, allowing the said first person to set an input condition to indicate that they are not home, so missed messages should not raise concern.

An anticipated objective of the present invention is to provide additional, and valuable customized services that are possible by integrating the present invention, (Assisting and Monitoring System), with other existing computer and telephony based services. Said additional valuable customized services as are not possible without the implementation of the present invention.

BRIEF DESCRIPTION OF THE DRAWINGS

The present invention is illustrated by way of example and not limitation in the accompanying figures, in which like references indicate similar elements, and in which:

FIG. 1 is a Block Diagram of a "Home Unit"—Reminder and Logging Device.

FIG. 2 is an example of memory record contents for a Home Unit.

FIG. 3 is an example of a Home Unit memory record file for event logs.

FIG. 4 is a Diagram of a Reminder and Logging and Notification System.

FIG. 5 is a Flow Chart for the Main Process of a Home Unit.

FIG. 6 is a Flow Chart for the Input Handling Subroutine.

FIG. 7 is a Flow Chart for the Reminder Handling Subroutine.

FIG. 8 is a Flow Chart for the Update & Diagnostics Subroutine.

FIG. 9 is a Flow Chart for the Outputting Subroutine.

FIG. 10 is a Flow Chart for the External Communications Subroutine.

FIG. 11 is a Diagram of an expanded Reminder and Logging and Notification System.

FIG. 12 is a Block Diagram of the Subscriber Communications Management System (SCMS) Device.

FIG. 13 is an example of an SCMS database table of subscriber profile records.

FIG. 14 is an example of possible SCMS database profile table record contents.

DETAILED DESCRIPTION OF THE INVENTION

In the description herein, numerous specific details are provided (such as examples of components and/or methods) to provide a thorough understanding of embodiments of the invention. One skilled in the relevant art will recognize, however, that an embodiment of the invention can be practiced without one or more of the specific details, or with other apparatus, systems, methods, components, materials, parts, and/or the like. In other instances, well-known structures, materials, or operations are not shown or described in detail to avoid obscuring aspects of embodiments of the invention.

An Assisting and Monitoring method and system for compliance logging and monitoring system for routine activities is presented as well as an automated communications/notification system that can relay the activity and/or inactivity recorded by a Home Unit device to other systems and/or specifically designated people.

A task reminder and completion monitoring system provides for convenient messages and/or reminders to alert person(s) to perform routine scheduled tasks and keeps record of task completion compliance. Task completion is determined by sensing for expected value(s) on input device(s), during a defined time period. In simplest form, this can be an input button on the Home Unit that is to be pressed upon task completion.

In its preferred embodiment the system includes network(s) and two-way communication devices to exchange information between remotely located event logging devices, (Home Units), and a central Subscriber Communications Management System, (SCMS). Each Home Unit has associated with it an account record in the SCMS. Each account record associated with a Home Unit user account contains pertinent subscriber profile information that includes records of who can access the account, and of the people that can access it, what permissions if any they have to make account profile changes. Parameters that can be changed, with proper permissions may include things like who, how and when members of a subscriber account are notified of Home Unit generated information. The SCMS performs the notification messaging by interfacing with the existing communications tools of the individual people or organizations associated with each Home Unit user account as are defined in the subscriber account profiles. Also, if specified, for certain conditions an emergency message can be sent to a monitoring facility and/or 911 call made by the SCMS or directly by the Home Unit. In this form it helps people or organizations care for and keep track of another person who may or may not be living with them.

The monitoring and notification service may also provide account access to one or more people as requested by the subscriber, these one or more people referred to as the account group associated with that subscriber. The subscriber can further request customized access permissions by person in the account group. For instance, subscribers can specify specific privileges by group member for both the programming sending of messages, alerts, and alert schedule updates to the Home Unit in that account, and for setting what notifications and messages they will receive from the system based on the communications from the Home Unit associated with their account. The system can provide these configuration options through a convenient interface, for example an Internet portal, a telephone voice prompt, and/or live telephone operator. The subscriber can request that other computer based systems be linked into their account, provided arrangements have been made between the monitoring and notification service and the other services' systems. In the system described here, a single Home Unit can provide reminders, two-way messaging and task completion tracking to one or more people; but, for ease of description it is presented here with reference to one or more people sending messages to and tracking task completion of one person per Home Unit.

FIG. 1 shows a block diagram of a Home Unit, (reminder and logging device) 100 and its major sub-components, 110, 120, 130, 140, 150, and 160. The controller module 110 includes a clock module that is aware of date, day of week, and time of day. The controller module is powered by a fail safe power supply module 120, which includes a backup internal rechargeable battery and external power supply that provides power for normal operation and maintains a charge on the battery for continuous operation—even in the absence of the external power source. The controller module 110 is also connected by a bus to an input module 130, an output module 140, a memory module 150, and a communications port 160.

The input module 130 interfaces to one or more input devices, which can be located within the unit or external to it. The input devices are connected to the input module by wired and/or wireless buses. The input devices can include sensors that automatically acquire input from their environment, such as motion detectors, water flow meters, and pressure sensors, as well as user interfaces that provide a means for an individual to directly enter information, for example push buttons, touch screens, microphones, cameras, magnetic card readers and RFID tag readers. Input signals captured by the input module are communicated over the bus to the controller module where they are processed according to pre-configured logical operations, including time date stamping the input information, categorizing it, and saving it to memory. The controller module 110 may also make functional decisions based on the input signal data values, time/date received, and pre-defined functional rules previously saved in the memory module 150, and accessed by the controller over the bus.

The output module 140 interfaces to one or more output devices, which can be located within the unit or external to it. The output devices are connected to the output module by wired or wireless buses. The output devices can provide audible, visual and/or physical signals to summon an individual that the Home Unit, 100 has determined that a condition exists that warrants their attention, such as a scheduled task is due to be performed, or a new message has arrived.

The memory module 150 has been configured with stored digital records necessary for operation of the Home Unit 100. Some of these records are general operations support needed by every such Home Unit, while many of these are user specific preferences and customizable operational mode choices. User specific settings include for example, a schedule of event times, communication messages, task reminder message contents, type of alerting output device(s) desired for each event, and rules for when the alert outputs should be activated or not. The event alerting rules can also be sensitive to one or more specific input conditions, present value, or input value at a referenced time interval, this being managed by the controller module 110. The memory module 150 also stores records that are generated by the controller module 110, and sent to it over the bus.

For ease of description, some arbitrary labels are given to memory module 150 stored records, as illustrated in FIG. 2. The memory record contents 200, are for illustrative purposes, and by no means exhaustive. One possible way the method described herein could be implemented is by utilizing memory stored contents categorized such as; Event Schedule 210, Message and Reminder Parameters 220, Input Parameters 230, and Output Parameters 240. Further, for the purpose of this description, and shown in FIG. 3, memory module 150 contains a section of memory where the controller module 110 logs all events 300, 310, 320, . . . 340 and event specific parameters according to time of occurrence. These logged events can be both input device initiated, or controller module initiated based on the master clock and predetermined scheduled expected event activities.

The controller module 110 continuously manages an Event schedule 210, while receiving and processing time sensitive input signals from the input module 130. Further, the controller module 110 decides when and which output devices the Home Unit 100 will exercise to summon an individual to action. The controller module 110 makes decisions based on the Event Schedule 210, time sensitive input signals from the input module 130, Message and Reminder parameters 220 and Output Parameters 240. Conditions may exist where all expected input signals would be detected at expected value and on schedule, and the Home Unit 100 would not have to exercise any output alerts, just simply generate and save event log records 300.

In other conditions, the controller module 110 will determine that it is time for a scheduled task, and that the input module 130 has not presented input signals that the controller module 110 deems as completion of the schedule task. The controller module 110 will alert the individual to task through the output module 140 based on the memory records 200, and will generate an event log record 300. The controller will repeat exercising the output devices, and generating event log records 300, until the input module 130 signals indicate that the individual has completed the task associated with the expected event or until a time limit or number of repeat alerts is reached, as defined in the memory record 200 for this scheduled event.

In some embodiments, it may be desired to include certain input types that are not schedule expected signal values, but have special influences on the controller module functionality. Such inputs could include an emergency call button, smoke detector etc. When these input signals present an alarm value to the controller module, it will take immediate specific action, such as triggering an emergency call, and/or sounding a fire alarm device. Other special inputs can be used to toggle functionality of the controller module, such as an input signal that indicates when an individual is present, or away. Naturally, it may be desirable for the rules for reminder alerts, and contents of reminder messages to be different when the individual is home verses away. Of course numerous variations are possible for handling of reminders for scheduled events that came due during the individual's absence and can be customized to the subscribers' preferences.

The primary function of the Home Unit 100 relates to the scheduling of future events and logging of events to that schedule. While a user interface could provide programming through the input module, and event log review could be possible through the output devices, that is not the preferred embodiment. In the preferred embodiment of this method the Home Unit 100 includes a communications port 160 for communications with an external device or system. In the preferred embodiment the Home Unit 100 can upload its event logs to an external device or system through the communications port 160. Further the Home Unit 100 can receive updated programming of memory parameters from the external device or system through the communications port 160. In a possible embodiment, it may be desirable for the Home Unit 100 to have a learning mode, where it learns the pattern of inputs based on time of day, day of week, etc, and builds its event schedule based on the learned patterns.

Shown in FIG. 4, in one possible embodiment, Home Unit(s) 100 are part of a reminding, logging and notification system where the Home Units are remotely located from a central Subscriber Communications Management System, SCMS, 420. In such a system, the Home Unit(s) 100 communicate with the SCMS 420 by wired or wireless means over a Network 410. It is possible that both the Home Unit(s) and the SCMS know the minimum expected times/ frequencies when the Home Unit should communicate with the SCMS. For example, the Home Unit could communicate the event logs every night to the SCMS, and check for new messages, appointments or tasks and associated reminders that were scheduled into the SCMS that day.

For illustration, one manner in which the Home Unit could perform its functions is illustrated in the flow charts provided in FIGS. 5-10. These flow charts are over simplifications of the actual process flow, and serve only for clarification of the functionality.

Input module 130 detects and presents input signals to the controller module 110. As shown at step S1000 in FIG. 5, the controller module continuously detects the presence of input signals. When an input signal is presented to the controller module 110, the controller module creates a time dated event log entry S1010 that is stored to the memory module 150, and then it starts the Input handling subroutine S1020. While detecting and handling input signals, the controller module simultaneously, or pseudo-simultaneously manages the Event schedule. Step S1030 in FIG. 5 shows the controller module 110 accesses the event schedule 210, and when a message or task reminder is due, step S1040 it starts the Reminder handling subroutine S1050, then performs the appropriate Outputting steps described in subroutine S1080. As described here in terms of events and reminders, the same process flow applies to two-way messages, surveys, and information exchange, just as a scheduled event where the message is handled like an associated reminder for the event. Likewise, responses to messages can be handled as the input associated with task completion tracking. The flow chart of FIG. 5 also symbolically represents that the function of the Home Unit 100 is continuous and never ending—as it is intended to be when in use. There will of course be some manner to program it into a "hibernate" or "off" mode where it does not generate outputs and waits dormant for reactivation signal conditions.

FIG. 5 also shows in steps S1030, S1040, S1060 and S1070, the controller module 110 can recognize when it is time to initiate updates and self-diagnostics, and then starts subroutine S1070 to perform these tasks. The Update and Diagnostics events/tasks include self-testing of the reminder-logging device critical functions such as, presence of external power source, back up battery conditions, access to communications network on the communications port 160, changes in the presence of input devices, as well as many internal self-tests of the memory and controller logic. Of course the output devices could be exercised in combination with the input devices to for example, generate an output tone and detect its presence and strength with an input microphone. Degradation or complete failure of any of these self-tests would then initiate an appropriate output signaling activity handled in the Outputting Subroutine S1080, FIG. 9. Likewise the controller module can determine from the Event schedule when it is time to initiate external communication with an external device or system over the communications port 160. This communication providing for the uploading of event logs 300, and the checking for updated programming of memory parameters 200, that can be received, verified, and accepted by the Home Unit 100, when appropriate.

FIG. 6 is a flow chart that further details the input handling subroutine S1020 functions of the controller module 110. When the controller module 110 logic operations determine to perform the Input handling subroutine, the controller accesses the Input parameters 230 from memory module 150, and at decision step S2010 checks if the Input type is of immediate action type/priority. If the input type is immediate action, then the controller module at step S2020 sets a variable for the communication type as Input initiated, and then at step 2040 returns to the process flow and calls the Outputting subroutine S1080. For example, certain input conditions may exist that are set for immediate action handling, such as a help button being pressed and may be defined to initiate the Home Unit 100 to immediately notify other people by way of communications over the communications port 160 with an external device or system that in turn notifies others.

More likely, for input signals generated that are not of immediate action, such as the user logging a response input for having completed a task on schedule, the Home Unit would not deem the input as Immediate action type. In this case of non immediate action, input handling at decision step S2010, then step S2030 follows where the controller module stores all input generated data to the event log record, 300, including the time and date of the input collection. All input signals must be handled in some such manner as to generate a memory record of both the input signals, and when they occurred, for use by the controller module 110. By making a record of the input signals and the time they occurred, the Home Unit 100, can determine when tasks have and have not been completed to schedule. Further, the Home Unit 100 uses the logged input information to make decisions on generating reminder alerts, and external communications, as are illustrated for example in the Reminder Handling subroutine S1050 and External Communications subroutine S4040.

FIG. 7 is a flow chart that details the Reminder Handling subroutine S1050 functions of the controller module 110. When the controller module 110 calls the Reminder Handling subroutine S1050, the controller module 110 accesses the Message and Reminder Parameters 220, and the Event Log records 300 as shown at steps 3010 and 3020. These parameters and stored log records contain the conditions and rules for the controller module to determine how to handle a scheduled event. At step 3030 the controller module decides if the scheduled event is a task that the user has already completed or not.

For instance, the schedule may show an expected event associated with the user pressing a response input button between 8 AM and 9 AM. Before the controller module starts reminding the user to press the button, the controller module checks if the proper response input button has already been pressed during the required time interval of 8 AM to 9 AM.

If the task has been completed, then in step S3040 the controller computes the Task compliance metrics; in this example, say task completed at 8:20 AM Feb. 15, 2001 without any reminder alerts delivered, and then at step S3050 this is recorded in the event log 300. If at step S3030 the task had not been completed, then at step S3060 the controller module 110 accesses the output parameters 240 associated with this scheduled event. Based on the Message and Reminder parameters 220, at step S3070 the controller decides if the conditions for delivering reminder alerts have been exceeded or not. For instance, a maximum number of reminder alerts delivered, and/or a maximum time passed event due for reminder alerts may be reached without the input signals being presented to the controller module to indicate the scheduled task was completed. In the case where the event has past without compliance and the maximum reminder alert conditions are reached, then at step S3080 the controller module computes the compliance metrics for this task, (for instance, task not completed by 9:30 AM even after 6 reminder alerts delivered every 5 minutes after 9:00 AM.) The controller module also sets a variable for the Communication type as Inactivity. The compliance metrics and communications type variable are recorded to the event log during the next step S3050. Subsequently, output devices are exercised, and/or external communications are executed as appropriate.

Returning to the Reminder Handling Subroutine FIG. 7, when at step S3070 the controller module decides the conditions exist to deliver reminder alerts, next at step S3090 the controller module checks if a time delay interval between repeat alerts associated with this task has been reached or not. For instance, if an input associated with a scheduled task is not received in the specified time interval, it can be specified to wait 5 minutes, 10 minutes, or 15 minutes etc, between repeated alerts to complete the task. If the delay between alerts has been reached, then at step S3100 pass variables are set to use in the Output subroutine S1080 where the output devices identified in the Message and Reminder parameters 220 will be exercised to summon the user to perform the scheduled task. For instance, flashing a light and playing a loud voice message, "Betty it is time to take your morning medications—please press the OK button after you have done this." When at step S3090 the delay between reminder alerts has not been reached, the controller module follows the process flow through subsequent steps without exercising any output devices on the next pass through the Outputting subroutine. The main process flow 500 will continue looping through for this schedule event generating reminder alerts at the set intervals until the event is deemed completed by input conditions presented, or the task is logged as failed due to non-compliance within the set conditions.

A simple variation of this process flow accommodates a set of outputting conditions associated with a single scheduled event. This is useful for instance, to activate one output device as a soft message reminder at a certain time relative to the event time, and then if the expected input is not sensed by a later time for this event, different output signaling is initiated. Further, the outputting device can be time limited or continuous, as selected in the Reminder Parameters 220. For example, an account member or authorized organization could set a text message to be displayed on a visual display interface that is part of a Home Unit. The message may be a reminder for an appointment for later that day, or a question about how they are feeling.

The message may call the subscriber to acknowledge the message, by inputting an answer of some sort. If the input is not registered in a defined time period, the Home Unit may be programmed for that event specifically to exercise additional output devices to get the subscriber's attention and further to execute external communications to others through the system.

While this description of the process flow implies handling one scheduled event at a time, the controller module 110 can manage multiple overlapping scheduled events.

In FIG. 5, the controller module reaches step S1060 when there are no new input signals to process and a user reminder or message is not due (S1040). At step 1060, if the controller module decides scheduled tasks are due for it to perform, it enters subroutine S1070; if not, it returns to the top of the main process flow 500.

FIG. 8 is the flow chart of the Update and Diagnostics Subroutine S1070. At step S4010 the controller module accesses the Event log records 300 and then decides (step S4020) if scheduled communications with external device(s) are due. When scheduled communications are due, at step S4030, the controller module sets a pass variable for the communications type to a value that represents a scheduled communications type, and then at step S4040 the External Communications Subroutine is called, after which process flow returns to the main process flow 500. When at step S4020 communications with external devices are not due, process flow continues with step S4050 where the controller module performs self test procedures. Results of the self-test are then recorded to the event log 300 by the controller module 110 at step S4060. Step S4060 also includes setting of output parameters based on the results of the self-test.

These parameters can then initiate appropriate output device signaling during the subsequent Outputting subroutine pass and/or external communications from calls within the same next Outputting subroutine pass when the appropriate conditions for such exist, as determined by the controller module 110. After step S4060, process flow returns to the main flow 500 and calls the Outputting subroutine S1080.

FIG. 9 is the flow chart of the Outputting Subroutine S1080. In the first step of the Outputting process flow S5010, the controller module 110 accesses the Memory parameters 200. The controller module then decides at step S5020 which if any of the output devices need to be activated. When appropriate the controller activates the specific output devices at step S5030 and then records the specifics of the activity into the event log, step S5040. In the case of reminder prompts, which output devices and the contents of the prompt can be passed into the subroutine through a combination of the Reminder Parameters 220 and the Output Parameters 240. For example, for an early morning prompt, a combination of flashing a light, and delivering a voice message over an amplified speaker could be delivered, where further, the reminder prompt is specific to that scheduled task being missed. For example, "Betty, this is your third reminder it's 9:15 AM, you haven't logged that you are up and OK yet, as you usually due before 9 AM." Next at step S5050 the controller module 110 checks if the outputting parameters to initiate external communications are set. These parameters include calls for external communications, as well as type and method of external communication desired. When external communications are due, the controller module 110 calls the External communications subroutine at step S5060. Otherwise, and after the External Communications subroutine, the controller module 110 returns to the main process flow 500, and continuously monitors for inputs to log and manages the schedule of events.

In FIG. 10 the subroutine for External Communications is further detailed. When process flow enters the External Communications subroutine at steps 6010 and 6020 the controller module 110 accesses the Memory parameters 200, and the event log records 300. The memory parameters contain information about which communication mechanisms to use, what types of communications are to be performed, what order to perform them, and what information will be sent and possibly received. In the next step, 6030 the controller module 110 tests the communications port to see if communications channel for the first communications method is available. If it is, then the controller module proceeds in step 6040 to perform the communications task. This step includes initiating communication, receiving acknowledgement that the desired receiving device or system has been reached, transmitting the appropriate data as specified in the memory parameters 200 and receiving confirmation that the transmitted data was received and deemed complete by embedded data consistency checks.

Further, the communication specifics may include that the Home Unit 100 also check with the receiving device for available memory updates from the receiving device. When such updates are deemed to exist, the communication step further includes that the Home Unit receive and store updated parameters for memory record 200, test the updated records for validity, and backup the existing set up records for auto recovery if the new records do not pass all self tests. The Home Unit will also send acknowledgement of a successful update, or indicate a failure to update if a problem exists with the new records or transfer thereof. After the communications are performed, in step 6050 the event log is updated, logging the communication that was just performed, and clearing off the oldest event logs that have been sent in to the external device and are no longer relevant to current and future Home Unit decisions. At step 6060 the controller module then reschedules any communications mechanisms that failed to complete for an appropriate future time and then returns to the main process flow 500.

At step 6030 if the communications channel desired is not available, then in step 6070 the controller module decides if additional communications mechanisms are specified for use related to this event. If other mechanisms are specified, the controller module switches to those in priority order, and repeats at step 6030. At step S6070 when there are no more communications mechanisms specified to use, and one or more specified communication mechanisms have not been completed, at step S6080 the controller module makes a determination to take corrective action step S6110 or just reschedule the external communications, step S6090. In step S6110 specifics related to the event that initiated the call for external communications are used to determine if the controller module 110 should exercise output devices to correct or summon the user to correct the problems with the communications channel(s).

For a high priority event such as a communication type that was input signal initiated, for instance, a call for help, the memory parameters may contain corrective action instructions, such as grabbing the phone line from a telephone that is deemed to be off the hook and caused the loss of a dial tone. Or for different circumstances, it may be preferred to take corrective actions dependent on time of day, and task compliance metrics. For instance, if all tasks are logged successfully on time, and it is mid day, the controller module could summon the user to check the phone lines, where if the same conditions occur but the phone line is dead at 3:00 A00 it may be preferred to delay summoning the user until after 8 AM. When corrective actions are appropriate, the controller module follows the flow chart in step S6110, then also can reschedule communications attempts step S6090 when appropriate. All activity is recorded to the event log at step S6100 before returning the process to the main flow 500.

In an example where corrective action is not chosen, for instance, the unit may not be able to access the communications line because it is in use. Typically for scheduled communications updates, when this occurs, the controller module would likely be set to not take corrective action, and proceed to step S6090 where it reschedules the communications to be reattempted at a near future time. Then the controller module records the event information in the event log, S6100 before returning to the main process flow 500. A maximum time delay of the line being in use could eventually trigger a corrective action, to ask the user if they are on the phone, and if everything is OK.

Shown in FIG. 4 Home Unit(s) 100 are part of a reminding, logging and notification system 400 where the Home Units are remotely located from a central Subscriber Communications Management System, SCMS, 420. The SCMS is a computer based system with an internal or external database 425, and it communicates over wired and/or wireless network(s) 411, with the conventional messaging devices of the caregivers associated with the Home Unit (reminder & logging) system subscribers. The SCMS provides the interfaces for convenient programming of the Home Unit 100, by Home Unit user, by the caregiver(s) of the user, or any individual or organization authorized by the subscriber. Programming can be accomplished by one of a number of methods such as telephone call to an operator, teleprompt entry, Internet web form entry and cooperative interaction with other computer based services.

A monitoring and notification service provider may offer to subscribers an ability to remotely deliver messages and scheduled event reminders within their subscriber account group, to track the completion of tasks associated with the scheduled events, and to receive convenient notifications based on customized conditions related to the logging of activities associated with the scheduled events, reminders or messages. For example, a subscriber may desire to set reminder prompts for future activities of daily living, track their compliance to performing tasks associated with the event schedule, and have status messages specific to the scheduled activities automatically delivered to a select group of people such as the caregivers of the individual using the Home Unit 100. Thus a member of an account group can use the service to deliver a message on a Home Unit, asking, "Betty, how do you feel today?" where Betty's response is automatically delivered to selected members of the account group. Such convenient messaging through the Home Units 100, enables a host of other possibilities.

A monitoring and notification service provider may offer additional services to its subscribers that become possible by linking the core functions illustrated in FIG. 4 with other computer or telephony based services and/or service provider systems. The monitoring and notification service provider may further offer these related and integrated services to other organizations that provide related value to the subscriber account groups associated with the Home Units in FIG. 4. FIG. 11 illustrates this possible expansion for clarification, not limitation.

FIG. 11 illustrates an expanded service offering which integrates with one or more related services that provide additional service or assist in the care of the Home Unit user/subscriber. In such an implementation, when one or more subscribers also receive service or care from another organization, they can opt for additional valued services only possible by linking in the related service providers' systems 460. Examples of related service providers that can be integrated with the Expanded Reminder Logging and Notifying System of FIG. 11 are described in the following sections for illustration, and not limitation.

A variation of the Assisting and Monitoring (Logging) Method and System includes a Pharmacy or Pharmacies in the Expanded Reminder Logging and Notifying System 10,000. Many value added services are possible, and a few are described here, not to limit but to illustrate. A subscriber of the monitoring and notification service could elect to include the Pharmacy in their profile as having permissions to set reminders for their Home Unit 100. The Pharmacy's computer systems 460 would have protocols and secure means to communicate with the SCMS 420. When a prescription is picked up, the pharmacy system can automatically inform the SCMS 420. The SCMS can then compare the medication schedule to the existing subscriber profile of medications and eating times and automatically update the reminders on the subscriber's Home Unit 100 to include reminders for this new medication. Further, if the medication has special requirements, to be taken with food for instance, the reminders can include that information and can automatically be set to coincide with the subscriber's profile of meal and medication times of day. Provided the Home Unit includes a visual display, images of the medication could accompany the reminders to further ensure the subscriber takes the correct medication(s).

With the Home Unit 100 tracking medication compliance, the SCMS 400 will also know when a maintenance prescription has reached the allowed refill point, typically the date when 80% should be used and can alert the subscriber, their family caregivers, and/or the pharmacy to obtain the refill before the medication is all gone. Like the customizable notification preferences, the reminder to refill can also be as desired, such as an email to a primary caregiver. The email can include the number of doses remaining and may include the Pharmacy phone/fax numbers and easiest way to initiate the refill process. This provides great convenience to the subscribers, their family caregivers, and the Pharmacy. Other Quality of care features are possible when a subscriber has all their pharmacies in the system. For instance, the pharmacy system could see all the existing medications that the individual currently has. This provides the opportunity for a cross check that a new medication will not have an adverse effect when taken with their other medications. This is an improved method of doing business for both the monitoring and notification service provider, and the Pharmacy. Providing this added service, the Pharmacy increases competitive value over other pharmacies and increases customer loyalty—not to mention the added value of keeping their clients healthier by helping them improve medication compliance.

Another example of an integrated service system 10,400 as part of the variation of the Assisting and Monitoring (Logging) Method and System FIG. 11 can include linked services with Care Coordinators and/or Professional Care Provider organizations in the Expanded Reminder Logging and Notifying System 10,000. Doing so brings value to more stakeholders, and provides opportunity to improve the quality of care that does not currently exist. Care coordinators include social workers, Area Agencies on Aging, (AAAs), and the Veterans Administration, among others. Professional Care Providers include but are not limited to: Doctors, Home Health Agencies (HHAs) and house keeping services. Care coordinators determine what services an individual should receive and what if any financial assistance can be provided. The care coordinators are responsible for overseeing the quality of care that professional providers give to the care recipients. Including them in the System 10,000 enables them to accurately track the time services are provided in the homes of the care recipients, to administer timely quality of service surveys shortly after the care is provided, and to provide new services not possible otherwise. Currently the AAAs rely on the care providers to also administer the quality of service surveys to the care recipients. The AAAs are aware that having the care provider ask the care recipients how satisfied they are with the services creates a tension that skews the results that the care recipients will report. The AAAs believe that if the Home Unit delivered the quality survey after the care provider left they would receive more accurate responses from the clients whose care services they oversee. Capturing the responses electronically further enables convenient reporting tools for the care coordinators and tracking metrics that enable on going quality improvements.

By linking the AAAs into the Expanded Reminder Logging and Notifying System 10,000, the subscribers that also receive care oversight from organizations like the AAAs can elect to include integrated services from the AAAs in their account profiles—thus enabling the AAA caseworkers to deliver and receive responses back from the subscribers through their Home Unit(s) 100 and the System 10,000. In addition to exchanging information with their elderly clients, the AAAs also need to communicate and exchange information with the family caregivers of their elderly clients. The System 10,000 accommodates communications with the entire subscriber account group, in this example the senior through the Home Unit, and the family members in their account group through their communications tools and preferences defined in the Account Profiles 8000.

Another example of how an organization like the AAAs can utilize these services is public service announcements. The Home Unit 100, can administer public service announcements to specific individuals based on their specific conditions. For instance, the PA dept of Aging informs a county AAA to notify everyone in their care with breathing difficulty of preventative steps they should take for a pending heat wave. The AAA must rely on phone calling to reach everyone in time. Including the AAA in the system, they can load the health prevention steps into the system and distribute to the select individuals with the pertinent condition. Further, the System can track which individuals acknowledged the health message and which did not. Thus, the system significantly reduces the number of individuals that must be reached in person. The AAAs can also use the system to administer depression surveys on the Home Units 100. This captures valuable data on the health of the individuals that the care coordinators are currently not staffed to collect, but acknowledge that having it would lead to improved outcomes for their clients.

A monitoring and notification service provider may integrate the SCMS with an Interactive Voice Response, (IVR), telephony system so as to offer a subset of the monitoring and notification services to certain subscribers where the care recipients receive scheduled interactive reminders and messaging over their telephones and/or cellular telephones. Integrating the SCMS with an IVR system enables the monitoring and notification service provider to offer some of the services described here to subscriber groups without requiring the presence of a Home Unit 100. The SCMS device or system will support database record and control process variations appropriate for this and similar service offering variations.

In its preferred embodiment the system includes one or more Home Units 100 that provide the features already described for the subscriber, and further provide a means for a care provider to input and output information at the location of the subscriber's Home Unit 100 that is shared with the system. This may be accomplished by input/output means that are internal or external to the Home Unit 100. In its preferred embodiment, the system includes at least one special input/output device, "Care Provider Tracking Box" (CPTB), preferably co-located with Home Units 100. This special device provides a separate interface for the care providers to input and retrieve information. Keeping the interfaces separate has added advantages and reduces possible confusion by keeping the Home Unit 100 user interface(s) as simple as possible for the subscribers (care recipients).

The CPTB communicates with the SCMS by wired or wireless means, directly, or though a subscriber's Home Unit 100. A check in logging device, the CPTB allows professional and/or informal care providers to log their activity at the home of an individual. The CPTB can utilize a secure means to identify the unique individual care provider when they arrive and when they leave. The CPTB can do this by passive or active means of care provider logging.

The CPTB is a specialized variation of the Home Unit 100 illustrated in FIG. 1. The particular difference being that the CPTB utilizes input and output mechanisms particularly designed to best facilitate the tasks and uses of the care providers in the care recipient's home or other facility. The input devices it includes enable a means of accurately logging the identity of one or more care providers and provide an easy entry of notes, record updates, and requests for follow up support action by the care provider themselves or by others. The output devices likewise are appropriate to support the tasks of the care providers at the residence of the care recipient, such as communicating updated information about client requirements to the care provider and prompting for system desired inputs from the care provider. The CPTB itself, or cooperatively with a Home Unit keeps time and date records of all CPTB input signals captured and output signals generated.

In one form for example, the CPTB would read a magnetic identity card, and prompt the care provider to sign their name on an electronic touch pad/screen, much like the credit card readers at checkout lines of retailers. Numerous other ways exist some of which are RF ID tag readers, keypads, etc. What is novel is collecting and delivering this information from and to care providers in the residence of the care recipient to assure better quality of care for the care recipient.

The use of such information that is made possible by the CPTB as part of the Expanded Reminder Logging and Notifying System 10,000 would directly benefit care coordinators such as AAAs, the Veterans Administration, and Home Health Agencies alike. Such information would also be valuable to family caregivers letting them know to take action to provide assistance when another caregiver has not performed at an expected and necessary time.

As part of the Expanded Reminder Logging and Notifying System 10,000, the CPTB communicates by wired or wireless means with the Subscriber Communications Management System (SCMS) device 420 directly or cooperatively with a Home Unit 100. Based on pre-defined rules stored in the Home Unit 100 and/or SCMS 420, and/or the CPTB itself, the information logged by the CPTB would trigger the Expanded Reminder Logging and Notifying System 10,000 to communicate in real time or at periodic reporting times, the information of the activities recorded by the CPTB to the family members and/or professional care organization(s) associated with the individual receiving care. The range of applications that this enables is quite broad. One would be notifying a loved one that an expected care provider has not arrived to provide assistance just minutes after that provider is past due. Another application would be reducing fraud by providing periodic reports of exact time and date of services provided by provider organization to the Care coordinators or Insurance Payer organizations. Numerous quality assurance applications can also be imagined that are made possible by such a CPTB included in the Expanded Reminder Logging and Notifying System 10,000.

FIG. 12 shows a generic block diagram of a Subscriber Communications Management System, (SCMS) 7000. The main components are a Controller 7010, a Database Interface 7020, Memory 7030, Network Interfaces 7040, Account management Interface 7050, Custom Hardware Interfaces 760, and a signal bus 7070.

The SCMS 7000 performs three key functions: communicates with Home Units 100 and CPTBs, generates custom notification messages to the communications tools of the caregivers and integrated service systems associated with each subscriber account, and provides convenient method(s) of updating event schedules, messages, reminder parameters, reminder contents, and operational parameters of the Home Units and CPTBs. Additionally, it can support numerous data analysis and reporting tools for the information collected by the Home Units, CPTBs, and connected communications tools of the account group members.

Each Home Unit 100 in the Expanded Reminder Logging and Notifying System 10,000 has associated with it a unique identification and a profile record stored in the database 425 of the Expanded Reminder Logging and Notifying System 10,000. The database 425 of the system may be accessed through the database interface 7020 or from the memory 7030. The place where the database is stored is dependent on specific implementation circumstances. For the following discussion, it is assumed that the database 425 is a storage device external to the SCMS device. The storage device may be distributed throughout the network 410. The SCMS device 420 may access the database 425 via the database interface 7020 through the network 410.

The database 425 may include a list 8000 of profiles 8010, 8020, 8030, and 8050 as shown in FIG. 13. Each profile 8010-8050 corresponds to a single Home Unit 100, and associated subscriber account. The SCMS device 420 performs its three key functions: communicates with Home Units 100 and CPTBs, generates custom notification messages to the communications tools of the caregivers and integrated service systems associated with each subscriber account, and provides convenient method(s) of updating event schedules, messages, reminder parameters, reminder contents, and operational parameters of the Home Units and CPTBs, as directed by each of the subscriber account profiles 8010-8050.

A generic example of the contents of a Profile record is provided in FIG. 14. The profile 8010 includes information such as unique identification 9010 of the associated Home Unit 100, event schedule of reminders 9020, reminder contents for scheduled events 9030, communications schedule 9040, Account Member Information 9050, Integrated Services parameters 9055, and Notification parameters 9060.

Returning to FIG. 12, the SCMS Controller 7010 manages periodic scheduled communications with the Home Unit(s) 100 by scanning the communications schedule 9040 of each of the profiles 8010-8050. Dependent on specific implementation circumstances, the SCMS device 420 may or may not be able to initiate communications with the Home Units 100.

In implementations where the SCMS device cannot initiate the communications with the Home Units 100, the Profile records 8010-8050 will contain specifics as to when the Home Unit is scheduled to initiate the communications and what Notification steps the SCMS device will perform if the Home Unit 100 does not make communications in the required time periods.

For instance, a Home Unit 100 may be installed where the only available communications channel is a Plain Old Telephone System, (POTS) line that is also the only phone line to the residence. The user may not care to be called every day by a computer-based system wishing to interface with the Home Unit 100. Instead, the user experience is better if the Home Unit 100 uses the phone line in the middle of the night to send in event logs and check for schedule updates.

In FIG. 11, when the SCMS Device 420 communicates with the Home Unit 100, it receives the Event log records 300 from the Home Unit, stores the received Event log records in the corresponding profile record 9000 associated with the specific Home Unit that generated the event log, sends updated memory records 200 to the Home Unit, performs verification of successful data receipt and transmission by cooperative action with the Home Unit, and reschedules future communications with the Home Unit as appropriate. The SCMS Device 420 also records Event log records 9080 of all its activity specific to each Home Unit Profile, 9000. Similarly the SCMS Device 420 communicates with CPTBs directly or through Home Units as appropriate for specific implementation requirements.

The second key function of the SCMS device 420 is to generate and deliver timely notification messages to the communications tools of the caregivers and integrated service systems associated with each of the Home Unit/subscriber account profiles 8010-8050. The SCMS controller 7010 scans the profile records 9000 of every profile, 8010-8050 and determines when, how and what notification messages should be delivered to each member or integrated service system of each subscriber account profile 8010-8050.

The SCMS device 420 performs a notification process that is appropriate for each of the notification methods.

For instance, one profile 8010 may have an event schedule 9020 of tasks with associated reminder alerts that are 2 to 4 per day, depending on day of the week, and a communication schedule 9040 that is daily between 2 AM and 4 AM and after any reminder alert that is not answered after the maximum retries with the user logged "Home". Further, the account member information 9050 contents of this profile 8010 may also include four caregivers associated with the one Home Unit at Betty's house. The primary caregiver, daughter Jane, may specify in the notification parameters that she wants an email sent to her every time the SCMS device 420 receives an update from Betty's Home Unit 100, and a text message to her cell phone any time the SCMS receives an immediate action initiated communication from the Home Unit, and after 5 AM any time the SCMS does not receive the expected daily communication (between 2 AM and 4 AM).

When Jane receives a notification message that Betty has not responded to reminder prompts and Betty is "Home", Jane can call Betty to assess if an emergency condition has occurred. Thus, the Reminder Logging and Notifying System 10,000 provides convenient reminders that improve compliance to activities of daily living, such as eating or taking medications, and enables a subscriber group to care for a loved one in a non-intrusive manner. The Reminder Logging and Notifying System 10,000 also provides for improved health for users of the Home Unit 100. Improved compliance to these types of activities (meals and medication) has been demonstrated to improve the health of elderly persons and individuals with chronic care needs.

Returning to the example of the customization of the notifications associated with a subscriber group, Jane's brother John, another caregiver in the account member information 9050 records associated with Betty's Home Unit, may want an email sent to him on the same conditions as Jane's. He may also specify an immediate phone call to his home and work numbers any time the Home Unit 100 communicates non-compliance events or scheduled communications between Betty's Home Unit 100 and the SCMS device 420 do not occur.

Betty may also have a life long friend Rose that although she lives too far away to help, wants to know that Betty is all right. In the account member information 9050 records, it may be specified for the SCMS device 420, to update a desktop status icon on Rose's personal computer. For example, the icon may be a green smiley face when everything is fine with Betty, yellow when Betty's compliance to tasks fails below a preset level, and a red frown when Betty's compliance to tasks falls below an even lower level. This helps Rose stay in touch, and is likely to prompt Rose to call Betty and ask how she's doing when things are not all smiles.

The profile 8010 associated with Betty's Home Unit 100, may further include a Health care provider in the account member information. For Betty's situation, it may not be desired for the health care provider to receive notifications, but rather to have access to history records, such as trend charts of task completion compliance associated with Betty's Home Unit recorded event logs. Further, it may be desired and stored in the profile record 8010 that this health care provider has permission to change the schedule of events and event reminder message contents, and that when any such changes are made, a summary report of the changes is delivered electronically to all caregivers by the methods also specified in the profile 8010.

Betty's primary care physician may have an appointment setting and reminder service that Betty has permitted limited access to her subscriber account. Doing so enables Betty to receive timely reminders for her doctor's appointments. The integrated service system can specify the reminder time of delivery, and request a time specific notice back if the appointment reminder is not answered in the necessary time period. Further, it can provide a yes/no choice of "can you keep this appointment" and take follow up actions that are dependent on the response that Betty provides through her Home Unit. The SCMS provides the notification updates processes to the integrated service systems as directed by Betty's account profile 8010.

The SCMS service provider may have tiered pricing dependent on the number of members per subscriber group, the number of integrated services, the number of messages delivered, the frequency of updates, the number of notifications and the types of notification methods desired by subscriber.

The third key function of the SCMS device 420 is to provide convenient method(s) of updating event schedules, messages, reminder parameters, reminder contents, and operational parameters of the Home Units and CPTBs. Every subscriber group will have at least one subscriber group member or integrated service organization with full permissions to modify Event Schedules 9020 (and any other parameters). Updates received by the SCMS are propagated to the appropriate Home Unit(s) and CPTB(s), by the SCMS when it performs its communication with the Home Units and CPTBs function. Updates to the SCMS can be accomplished by automated or semi-automated cooperation with other computer based system services, or by a member calling the SCMS service provider, or by telephoning a voice prompt system, or by logging on to the SCMS device 420 via the internet, for example, and editing their account profile such as Betty's profile 8010.

The SCMS device 420 supports an update process that is appropriate for each of the update methods.

This SCMS system 10,000 also provides a convenient way to share messages with a subscriber group. For instance, when Betty is leaving to run errands, she may press an "Away" input button on her Home Unit 100, and then record a voice message input. The communication schedule parameter settings may also include settings for the Home Unit to initiate communication shortly after Betty records a message. Betty goes about her errands, while her Home Unit 100 communicates her status and recorded message to the SCMS device 420. By the time Betty is off the driveway and headed into town, the SCMS device has logged the updates from Betty's Home Unit 100, determined who in Betty's account member information 9050 wants to be notified and is notifying them by the appropriate notification methods.

Betty is not trapped at home trying to call a loved one to let someone know she is going out. If a loved one that hasn't elected to be notified for these conditions calls and is worried that Betty does not answer, that loved one can log on to a private internet page and check Betty's status and hear the message she left. Alternately, the status could also be checked by a phone call to the SCMS service provider, or touch-tone voice prompt system that provides the same information.

In a simple form for example, a Home Unit of the system would have three large buttons, labeled "OK", "HOME", and "AWAY". This unit would be located in the home of an elderly person. The unit would be programmed for expected time and day activities either by a remote system, or by using a learning mode to study the logging activity during initial setup. When the time arrives for an expected logging of an "OK" event and the current status indicates a "HOME" condition, and if the Home Unit hasn't received an OK button pressed input signal after a preset delay, it will prompt the elderly person and ask them if they have completed the task. The Home Unit will continue prompting the elderly up to a preset amount of time, or number of reminder alerts, until the input signal is received. If the limit is reached without receiving the input signal, the Home Unit will communicate to the SCMS, which will in turn take the notification steps in the account profile settings—such as who, when, and how to notify when a task is not logged and the individual is home.

In this example, when the "OK" button is pressed as expected, the Home Unit can either communicate the "OK" event shortly after each "OK" event is logged, or communicate all log events at a later scheduled recurring time, say every morning. Likewise with the changes in AWAY and HOME conditions, these can be communicated right after each change in Condition, or at a later scheduled time. The Home Unit could include the logic circuitry to change its behavior based on certain inputs, such as the HOME/AWAY condition. For instance, if desired, the Home Unit can still give reminder alerts for tasks that come due during an "AWAY" logged condition, but not necessarily send an elevated concern communication that may be desired when the "OK" is missed and the condition is "HOME". All such choices can be managed by the caregivers of the elderly through a remote access network to the SCMS and updated automatically to the specific Home Unit. The SCMS can also provide the ability for the caregivers to voice record messages that will be later delivered to the Home Unit. This can be for the recurring alert message(s), or for one-time voice messages, delivered at a selected future time range and HOME status.

The present invention is a method for assisting and monitoring a person's compliance to complete certain tasks based on logging of task completion and convenience reminders comprising: generating an event log of the person's activities by monitoring and time based recording signals from at least one input mechanism, providing time sensitive reminders to alert the person of tasks they need to complete, comparing the activity event log to the task event schedule to create a compliance metric associated with every scheduled task, providing a capability for periodic review of the recorded input signals and computed compliance metrics, and including a capability to update memory contents, with updated event schedules, profile preferences, and messages. The method includes a stored profile which allows one or more input signals to modify the functionality of the reminder alerts and compliance decisions related to time based expected signal inputs. The method includes input mechanisms that includes a voice recorder that allows for the person to dictate and store a voice message. The method includes output mechanisms which include a capability to audibly play voice messages at specified times. The method includes the capability for periodic event log review and memory content updates that comprise communicating part or all of the activity log over a wired or wireless network to an external device, receiving acknowledgement of successful communications over the network from the external device and receiving updated memory settings for profile preference settings, messages, reminder alerts and schedules. The method includes the capability for periodic event log review and memory content updates further comprising: performing a self-test on the received updates message, sending a confirmation signal of a successful update over the network to the external device, and restarting the communication transactions if any part is not confirmed as successful. The method includes features whereby communication is initiated by the Home Unit based on stored profile settings that trigger the communication activities based on scheduled times, certain input signal combinations, the lack of expected input signals during scheduled times, and/or select combinations of such. The method includes features whereby the communication is initiated by an external device or system based on stored profile settings that trigger the communication activities based on scheduled times, lack of expected communications from the Home Unit, programming updates performed by account users through the SCMS Account management Interface, programming updates initiated by other computer based systems and/or select combinations of such. The method includes features whereby the capability for periodic event log review and memory content updates comprises: communicating part or all of the activity log over a wired or wireless network to an external device, receiving acknowledgement of successful communications over the network from the external device, and reinitiating the communication if the acknowledgement of successful communications is not received. The method includes features whereby the capability for periodic event log review and memory content updates comprises: communicating a ready to receive updates status over a wired or wireless network to an external device, receiving updated memory settings for profile preference settings, messages, reminder alerts and schedules, performing a self test on the received updates message, and sending a confirmation signal of a successful update over the network to the external device.

The present invention is also a system that assists and monitors a person's compliance to complete certain tasks based on logging of task completion, convenience reminders and messages, and group notification tools comprising: a controller generating an event log of the person's activities by monitoring and recording signals from at least one input mechanism, recording time of occurrence records with the input signal(s), providing time sensitive reminders to alert the person of tasks they need to complete, comparing the activity event log to the task and task reminder schedule to create a compliance metric associated with scheduled tasks, coupled to a network, wherein the event logs of input signals and task compliance metrics can be communicated over a network to conventional messaging tools based on customized settings stored in the corresponding user profile. The system includes features whereby a stored profile allows that one or more input signals can modify the functionality of the Home Unit alerts and compliance decisions related to time based expected signal inputs. The system includes features whereby the input mechanisms include a voice recorder that allows for the person to dictate and store a voice message. The system includes features whereby the output mechanisms include a capability to audibly play voice messages at specified times. The system includes features whereby the Home Unit communicates part or all of the activity log over a wired or wireless network to a Computer based Subscriber Communications management System, receives acknowledgement of successful communications from the SCMS, and may at times also receive updated memory settings for the Home Unit from the SCMS. The system includes features whereby the Home Unit further performs a self-test on the received updates message, sends a confirmation signal of a successful update over the network to the SCMS, and restarts the communication transactions if any part is not confirmed as successful. The system includes features whereby the communication is initiated by the Home Unit based on stored profile settings that trigger the communication activities based on scheduled times, certain input signal combinations, the lack of expected input signals during scheduled times, and/or select combinations of such. The system includes features whereby the communication is initiated by the SCMS based on stored profile settings that trigger the communication activities based on scheduled times, lack of expected communications from the Home Unit, programming updates performed by account users through the SCMS Account management Interface, programming updates initiated by other computer based systems, and/or select combinations of such. The system includes features whereby the Home Unit(s) further include the capability to provide intercom communications between other Home Units, and/or pre-selected cellular phones, the exact Home Unit logging devices and cellular phones in an intercom group being stored in a profile setting within the Home Unit(s), and/or SCMS. The system includes features whereby the intercom communications are supported over the existing Cellular Telephone system infrastructure. The system includes features whereby the intercom communications are supported by direct unit-to-unit wireless methods. The system includes features whereby the intercom communications are supported over the existing Paging system infrastructure. The system includes features whereby the intercom communications are supported over the existing Telephone system infrastructure. The system includes features whereby the intercom communications are supported over the existing CATV system infrastructure. The system includes features whereby the intercom communications are supported over the existing Satellite infrastructure.

While different embodiments of the invention have been described in detail herein, it will be appreciated by those skilled in the art that various modifications and alternatives to the embodiments could be developed in light of the overall teachings of the disclosure. Accordingly, the particular arrangements are illustrative only and are not limiting as to the scope of the invention which is to be given the full breadth of any and all equivalents thereof.

I claim:

1. A method for assisting and monitoring a person's compliance to complete certain healthcare tasks, and simultaneously providing an automated communication tool to other persons or systems comprising:

generating an activity event log of data pertaining to the person's healthcare-compliance activities by monitoring and time-based recording of signals from at least one input mechanism;

providing a task reminder schedule containing time-sensitive reminder alerts to alert the person of scheduled healthcare tasks they need to complete;

comparing the activity event log to the task reminder schedule to create a compliance metric associated with every scheduled healthcare task;

communicating selective parts of the activity event log and compliance metrics to other persons or systems;

providing a capability for periodic review of the data pertaining to the time-based recorded signals and computed compliance metrics in said activity event log; and providing a capability to update memory contents, with an updated task reminder schedule, profile preference settings, and digital messages.

2. The method of claim 1, further comprising storing a user profile for said person, wherein said stored user profile allows one or more input signals to modify the functionality of the reminder alerts and compliance decisions related to time based expected signal inputs.

3. The method of claim 2, wherein the capability for periodic activity event log data review and memory content updates includes communication activities comprising:

performing a communication transaction to communicate part or all of the activity event log data over a wired or wireless network to an external device;

receiving acknowledgement of successful communication of the activity event data over the network from the external device;

receiving updated memory settings for profile preference settings, digital messages, reminder alerts and scheduled healthcare tasks and generating a received updates message;

performing a self test on the received updates message to identify the occurrence of a successful update;

sending a confirmation signal of a successful update over the network to the external device when a successful update has occurred; and restarting the communication transactions if any part of the communication transaction is not confirmed as successful.

4. The method of claim 3 where the communication transaction is initiated by a Home Unit and comprises stored profile settings that trigger the communication activities based on scheduled times, certain input signal combinations, the lack of expected input signals during scheduled times, and/or select combinations of such.

5. The method of claim 3, wherein said other persons include account users, where the communication transaction is initiated by an external device or system and comprises stored profile settings that trigger the communication activities based on scheduled times, lack of expected communications from a Home Unit, programming updates performed by said account users through the external device or a system account management interface, programming updates initiated by other computer based systems, and/or select combinations of such.

6. A system that assists and monitors a person's compliance to complete certain healthcare tasks based on logging of healthcare task completion, healthcare-task reminders, and group notification tools comprising:

a controller generating an activity event log of data pertaining to the person's healthcare activities by monitoring and recording signals from at least one input mechanism, recording time-of-occurrence records with the input signal(s), a healthcare-task reminder schedule containing time-sensitive healthcare-task reminders to alert the person of healthcare tasks they need to complete, comparing the activity event log to the healthcare task reminder schedule to create a compliance metric associated with scheduled healthcare tasks, coupled to a network, wherein the activity event log data and task compliance metrics can be communicated over the network to conventional messaging tools based on customized settings stored in a user profile corresponding to the person.

7. The system of claim 6 where said user profile allows one or more input signals to modify the functionality of the reminder alerts and compliance decisions related to time based expected signal inputs.

8. The system of claim 7 where said at least one input mechanism includes a voice recorder that allows the person to dictate and store a voice message.

9. The system of claim 7, further comprising one or more output mechanisms where the output mechanisms include a capability to audibly play voice messages at specified times.

10. The system of claim 7, further comprising at least one Home Unit, wherein said at least one Home Unit communicates part or all of its activity event log data over a wired or wireless network to a Computer based Subscriber Communications Management System (SCMS), receives acknowledgement of successful communications from the SCMS, and may at times also receive updated memory settings for the Home Unit from the SCMS.

11. The system of claim 10, wherein the one or more Home Units further perform a self-test on the received updates message, sends a confirmation signal of a successful update over the network to the SCMS; and restarts the communication transactions if any part is not confirmed as successful.

12. The system of claim 11 where the communication is initiated by the Home Unit, said communication comprising profile settings that trigger the communication activities based on scheduled times, certain input signal combinations, the lack of expected input signals during times during which a healthcare task is scheduled, and/or select combinations of such.

13. The system of claim 11 where the communication is initiated by an external device or system, said communication comprising profile settings that trigger the communication activities based on scheduled times, lack of expected communications from the Home Unit, programming updates performed by account users through the external device or system account management interface, programming updates initiated by other computer based systems, and/or select combinations of such.

14. The system of claim 10 where the communication is initiated by the Home Unit and comprises profile settings that trigger the communication activities based on scheduled times, certain input signal combinations, the lack of expected input signals during times during which a healthcare task is scheduled, and/or select combinations of such.

15. The system of claim 10 where the communication is initiated by an external device or system, said communication comprising profile settings that trigger the communication activities based on scheduled times, lack of expected communications from the Home Unit, programming updates performed by account users through the external device or system account management interface, programming updates initiated by other computer based systems, and/or select combinations of such.

16. The system of claim 6 where the Home Unit(s) further include the capability to provide intercom communications between other Home Units, and/or pre-selected cellular telephones that are grouped into one or more intercom groups; the exact Home Units and cellular telephones in an intercom group being stored in a profile setting within the Home Unit(s), and/or SCMS.

17. The system of claim 16 where the intercom communications are supported over an existing Cellular Telephone system infrastructure.

18. The system of claim 16 where the intercom communications are supported by direct unit-to-unit wireless methods.

19. The system of claim 16 where the intercom communications are supported over an existing Paging system infrastructure.

* * * * *